(12) United States Patent
Takamatsu

(10) Patent No.: US 8,674,231 B2
(45) Date of Patent: Mar. 18, 2014

(54) ENDOSCOPE

(75) Inventor: Masaki Takamatsu, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 75 days.

(21) Appl. No.: 13/523,769

(22) Filed: Jun. 14, 2012

(65) Prior Publication Data

US 2013/0008694 A1 Jan. 10, 2013

(30) Foreign Application Priority Data

Jul. 6, 2011 (JP) ................................ P2011-150253

(51) Int. Cl.
*H05K 1/18* (2006.01)
(52) U.S. Cl.
USPC ............ 174/250; 174/261; 174/267; 361/816
(58) Field of Classification Search
USPC ........ 174/33, 34, 36, 102 R, 103–104, 105 R, 174/107, 110 R, 113 R, 250, 261, 267; 361/777, 748, 767, 816–818
See application file for complete search history.

(56) References Cited

U.S. PATENT DOCUMENTS

| | | | |
|---|---|---|---|
| 6,882,542 B2 * | 4/2005 | Tamaki et al. ................ | 361/760 |
| 2002/0050386 A1 * | 5/2002 | Aizawa et al. .............. | 174/74 R |
| 2010/0231250 A1 * | 9/2010 | Breinlinger et al. .......... | 324/760 |
| 2010/0231702 A1 * | 9/2010 | Tsujimura et al. ............. | 348/65 |
| 2011/0220389 A1 * | 9/2011 | Huang et al. .............. | 174/113 R |
| 2013/0248222 A1 * | 9/2013 | Inaba et al. ................... | 174/107 |

FOREIGN PATENT DOCUMENTS

| | | | | |
|---|---|---|---|---|
| JP | 2000-125161 A | | 4/2000 | |
| JP | 2000125161 A | * | 4/2000 | ............ H04N 5/225 |
| JP | 2003045244 A | * | 2/2003 | ............ H01B 11/18 |
| JP | 2006185741 A | * | 7/2006 | |
| JP | 2008124590 A | * | 5/2008 | |
| JP | 2009-082504 A | | 4/2009 | |
| JP | 2010-068930 A | | 4/2010 | |
| JP | 2010068930 A | * | 4/2010 | |

* cited by examiner

*Primary Examiner* — Hoa C Nguyen
*Assistant Examiner* — Amol Patel
(74) *Attorney, Agent, or Firm* — McGinn IP Law Group, PLLC

(57) ABSTRACT

Provided is an endoscope in which the work of connecting cables to a circuit board in the distal end of an insertion part can be easily performed. When a bundle-wire cable obtained by bundling a plurality of single-wire cables and a plurality of coaxial cables are connected to a circuit board arranged at the distal end of an insertion part, terminals that connect cores of the single-wire cables, terminals that connect cores of the coaxial cables, terminals that connect shields of the coaxial cables, and terminals that connect the shield of the bundle-wire cable are arranged in tandem at predetermined intervals on the common plane of the circuit board.

20 Claims, 15 Drawing Sheets

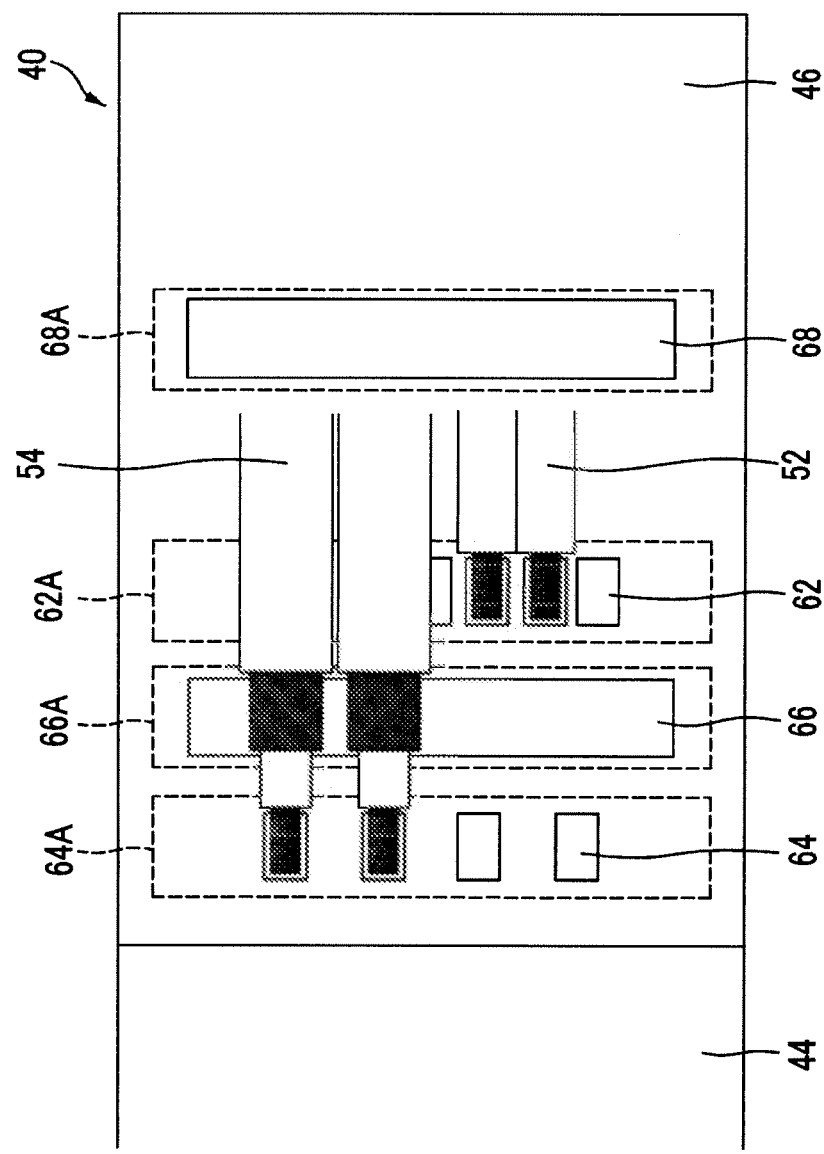

ENDOSCOPE

BACKGROUND OF THE INVENTION

1. Field of the Invention

The present invention relates to an endoscope, and particularly, to a connection structure of a cable to a circuit board built into a distal end of an insertion part of an endoscope.

2. Description of the Related Art

In electronic endoscopes, an imaging element is built into the distal end of an insertion part. The imaging element is mounted on a circuit board, and transmission of a video signal or the like is performed via a cable connected to the circuit board.

Generally, a bundle-wire cable obtained by bundling a plurality of single-wire cables and a plurality of coaxial cables is used as the cable. In recent years, coaxial cables tend to be frequently used from the viewpoint of improving transmission characteristics.

However, since both the shields and cores of the coaxial cable should be connected (for example, JP2010-68930A or the like), when the number of the coaxial cables is increased, there are problems in that the number of connecting terminals to be formed on the circuit board is also increased, and promotion of a smaller diameter is hindered.

For this reason, in the related art, for example, a configuration in which the coaxial cables and the single-wires cable are divided and connected above and below a circuit board (front and rear) has been proposed (for example, JP2010-68930A and JP2000-125161A).

However, in the configuration in which the coaxial cables and the single-wire cables are divided and connected above and below the circuit board, there are drawbacks in that the wiring should be divided, connection work should be performed after being divided to the front and rear of the circuit board, and time and effort are required for the wiring connection work. In order to separate and connect the cables, there is also a drawback that the strength of a connecting portion becomes weak.

JP2009-82504A is an example of related art.

SUMMARY OF THE INVENTION

The present invention has been made in view of the above-mentioned problems and an object of the present invention is to provide an endoscope in which the work of connecting cables to a circuit board in the distal end of an insertion part can be easily performed.

The means for solving the above problems is as follows.

[1] An endoscope of a first aspect includes: an insertion part; a circuit board arranged in a distal end of the insertion part; a bundle-wire cable including a plurality of single-wire cables that are bundled together, a plurality of coaxial cables that are bundled together along with the plurality of single-wire cables, a bundle-wire shield that covers the periphery of the plurality of single-wire cables and the plurality of coaxial cables that are bundled together, and a bundle-wire covering that covers the periphery of the bundle-wire shield, arranged within the insertion part, and connected to the circuit board, a plurality of single wire connecting terminals provided in the single wire connecting terminal forming region of the circuit board and having cores of the plurality of single-wire cables individually connected to the plurality of single wire connecting terminals; a plurality of coaxial core connecting terminals provided in the coaxial core connecting terminal forming region of the circuit board and having cores of the plurality of coaxial cables individually connected to the plurality of single wire connecting terminals; a coaxial shield connecting terminal provided in the coaxial shield connecting terminal forming region of the circuit board and having shields of the plurality of the coaxial cables connected thereto; and a bundle-wire shield connecting terminal provided in the bundle-wire shield connecting terminal forming region of the circuit board and having the bundle-wire shield connected thereto. The single wire connecting terminal forming region, the coaxial core connecting terminal forming region, the coaxial shield connecting terminal forming region, and the bundle-wire shield connecting terminal forming region are arranged in a common plane, and are arranged side by side in a column at predetermined intervals on a common straight line.

According to the first aspect, the forming region of the single wire connecting terminals (single wire connecting terminal forming region) for connecting the cores of the single-wire cables, the forming region of the coaxial core connecting terminals (coaxial core connecting terminal forming region) for connecting the cores of the coaxial cables, the forming region of the coaxial shield connecting terminals (coaxial shield connecting terminal forming region) for connecting the shields of the coaxial cables, and the forming region of the bundle-wire shield connecting terminals (bundle-wire shield connecting terminal forming region) for connecting the bundle-wire shield are arranged in the common plane, and are arranged side by side in a column at predetermined intervals on common straight line. That is, the forming regions of the respective connecting terminals are arranged side by side back and forth in the axial direction of the bundle-wire cable. Here, the "being arranged in a column" means that the forming regions of the respective connecting terminals are arranged to extend in a direction orthogonal to the axial direction of the bundle-wire cable. Thereby, the width of the forming regions of the respective connecting terminals required for the circuit board (width in the direction orthogonal to the axial direction of the bundle-wire cable) can be suppressed, and the circuit board can be miniaturized. Additionally, since the forming regions of the respective connecting terminals are arranged on the common plane, connection of the respective cables can be collectively performed on the common plane. Moreover, connection work can also be easily performed simply by adjusting the lengths of the respective cables in conformity with the forming positions of the corresponding connecting terminals and performing covering peeling processing or simply by connecting the respective cables side by side on the circuit board (laser welding, soldering, or the like).

[2] An endoscope of a second aspect includes: the plurality of single wire connecting terminals are arranged in parallel at predetermined intervals in a direction orthogonal to the straight line and are arranged symmetrically with respect to the straight line, and the plurality of coaxial core connecting terminals are arranged in parallel at predetermined intervals in the direction orthogonal to the straight line and are arranged symmetrically with respect to the straight line in the endoscope of the first aspect.

According to the second aspect, the plurality of single wire connecting terminals formed in the single wire connecting terminal forming region are arranged in parallel at predetermined intervals in the direction orthogonal to the axis of the bundle-wire cable and are arranged symmetrically with respect to the axis of the bundle-wire cable. Similarly, the plurality of coaxial core connecting terminals formed in the coaxial core connecting terminal forming region are arranged in parallel at predetermined intervals in the direction orthogonal to the axis of the bundle-wire cable and are arranged symmetrically with respect to the axis of the bundle-wire cable. Thereby, the widths of the single wire connecting terminal forming region and the coaxial core connecting terminal forming region in the axial direction of the bundle-wire cable can be suppressed, and the circuit board can be miniaturized. Additionally, connection work can also be performed easily by being arranging symmetrically. Moreover, the cores and shields of the respective coaxial cables can be connected together close to each other, and the shielding effect can be improved.

[3] An endoscope of a third aspect includes: the plurality of single wire connecting terminals are arranged at the same intervals as the arrangement intervals of cores of the respective single-wire cables when the plurality of single-wire cables are placed side by side on the circuit board, and the plurality of coaxial core connecting terminals are arranged at the same intervals as the arrangement intervals of cores of the coaxial cables when the plurality of coaxial cables are placed side by side on the circuit board in the endoscope of the second aspect.

According to the third aspect, the plurality of single wire connecting terminals formed in the single wire connecting terminal forming region are arranged at the same intervals as the arrangement intervals of the cores of the respective single-wire cables when the plurality of single-wire cables are placed side by side on the circuit board. Similarly, the plurality of coaxial core connecting terminals formed in the coaxial core connecting terminal forming region are arranged at the same intervals as the arrangement intervals of the cores of the respective coaxial cables when the plurality of coaxial cables are placed side by side on the circuit board. Thereby, the alignment between the respective cores and the respective connecting terminals can be performed and connection work can be performed easily, simply by arranging the single-wire cables and the coaxial cables on the circuit board.

[4] An endoscope of a fourth aspect includes: the coaxial shield connecting terminal is provided in a belt shape in a direction orthogonal to the straight line, and the bundle-wire shield connecting terminal is provided in a belt shape in the direction orthogonal to the straight line in the endoscope of the second or third aspect.

According to the forth aspect, both the coaxial shield connecting terminals formed in the coaxial shield connecting terminal forming region and the bundle-wire shield connecting terminals formed in the bundle-wire shield connecting terminal forming region are provided in a belt shape in the direction orthogonal to the axis of the bundle-wire cable. Thereby, the widths of the coaxial shield connecting terminal forming region and the bundle-wire shield connecting terminal forming region in the axial direction of the bundle-wire cable can be suppressed, and the circuit board can be miniaturized. Additionally, the cores and shields of the respective coaxial cables can be connected together close to each other, and the shielding effect can be improved.

[5] An endoscope of a fifth aspect includes: the circuit board has a bundle-wire covering connecting portion that connects the bundle-wire covering in the endoscope of any one of the first to fourth aspects.

According to the fifth aspect, the bundle-wire covering connecting portion that connects the bundle-wire covering to the circuit board is provided. Thereby, the bundle-wire cable can be connected to the circuit board, and the strength of the connecting portion between the bundle-wire cable and the circuit board can be secured.

[6] An endoscope of a sixth aspect includes: the single wire connecting terminal forming region, the coaxial core connecting terminal forming region, the coaxial shield connecting terminal forming region, and the bundle-wire shield connecting terminal forming region are arranged in a column at predetermined intervals on the straight line in this order from a distal end side of the insertion part in the endoscope of any one of the first to fifth aspects.

According to the sixth aspect, the forming regions of the respective connecting terminals are arranged in a column on the circuit board in the order of the single wire connecting terminal forming region, the coaxial core connecting terminal forming region, the coaxial shield connecting terminal forming region, and the bundle-wire shield connecting terminal forming region from the distal end side of the insertion part. By arranging the single wire connecting terminal forming region of the single-wire cables ahead of the coaxial core connecting terminal forming region and coaxial shield connecting terminal forming region of the coaxial cables, routing of the cables becomes easy and connection work can be performed more easily. Additionally, the shielding effect of the coaxial cables can be enhanced by closely arranging the coaxial core connecting terminal forming region and coaxial shield connecting terminal forming region of the coaxial cables. Additionally, connection work can also be preformed collectively, and the connection work can be performed easily.

[7] An endoscope of a seventh aspect includes: the circuit board is constituted by a flexible printed circuit board, and a cable connecting portion where the single wire connecting terminal forming region, the coaxial core connecting terminal forming region, the coaxial shield connecting terminal forming region, and the bundle-wire shield connecting terminal forming region are provided, and an electronic component mounting portion where electronic components are mounted are formed, and are adapted so as to be capable of being folded back in the endoscope of any one of the first to fifth aspects.

According to the seventh aspect, the circuit board is formed by a printed circuit board, and is adapted to be capable of being folded back. Since the respective cables are connected only to one side of the cable connecting portion, the cable connecting portion and the electronic component mounting portion can be overlappingly arranged. This can further miniaturize the circuit board.

According to the invention, the bundle-wire cable constituted by the single-wire cables and the coaxial cables can be simply connected by the circuit board built into the distal end of the insertion part.

BRIEF DESCRIPTION OF THE DRAWINGS

FIG. 11 is a view showing another example of an array of connecting terminals.

DESCRIPTION OF THE PREFERRED EMBODIMENTS

A preferable embodiment of the invention will be described below according to the accompanying drawings.

[Overall Configuration of Endoscope System]

Figure 1:
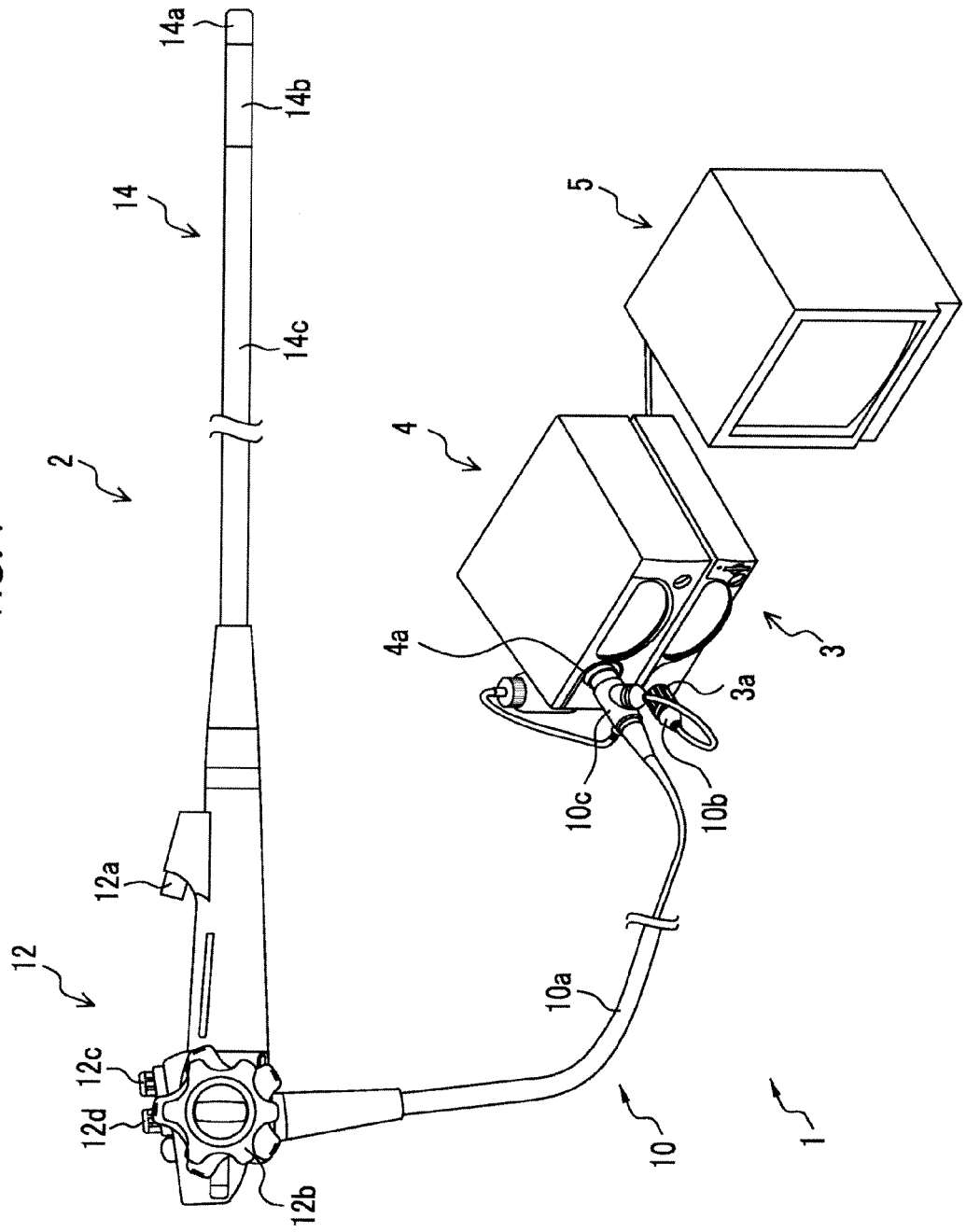
FIG. 1 is a view showing one embodiment of the system configuration of an endoscope system.

FIG. 1 is a view showing one embodiment of the system configuration of an endoscope system.

As shown in this drawing, the endoscope system 1 is mainly constituted by an endoscope (electronic endoscope) 2 that images the inside of a body cavity of a subject, a processor device 3 that generates an image within the body cavity on the basis of a signal obtained by imaging, a light source device 4 that supplies light with which the inside of the body cavity is irradiated, and a monitor 5 that displays an image within the body cavity.

The endoscope 2 is mainly constituted by a connecting part 10 for connection with the processor device 3 and the light source device 4, a manipulating part 12 for performing various kinds of manipulation, and an insertion part 14 to be inserted into a body cavity.

The connecting part 10 is constituted by a universal cord 10a, and is connected to the manipulating part 12. A distal end of the universal cord 10a is provided with a processor connector 10b for connection with the processor device 3 and a light source connector 10c for connection with the light source device 4. The endoscope 2 is connected to the processor device 3 by connecting the processor connector 10b to a connector 3a provided at the processor device 3. Additionally, the endoscope is connected to the light source device 4 by connecting the light source connector 10c to a connector 4a provided at the light source device 4.

The manipulating part 12 is formed in such a form that an operator can grip it with a single hand, and includes a forceps inlet 12a for inserting a treatment tool, an angle knob 12b for manipulating to curve the distal end of the insertion part 14 in the up-and-down direction and the right-and-left direction, an air and water supply button 12c for jetting air or washing liquid from an air and water supply nozzle 30 provided at the distal end of the insertion part 14, and a suction button 12d for suction from the forceps outlet 28 provided at the distal end of the insertion part 14, or the like.

The insertion part 14 is formed in a tubular shape, and is constituted by a distal end portion 14a, a curvable portion 14b, and a flexible tube portion 14c sequentially from the distal end thereof.

The distal end portion 14a is formed of a rigid metallic material or the like, and has an imaging element or the like built therein.

The curvable portion 14b is provided in a curvable manner, and is operated to curve in the up-and-down direction and the right-and-left direction by the manipulation of the angle knob 12b of the manipulating part 12.

The flexible tube portion 14c is configured to have flexibility, and is coupled to a distal end of the manipulating part 12. Most of the insertion part 14 is constituted by the flexible tube portion 14c.

Figure 2:
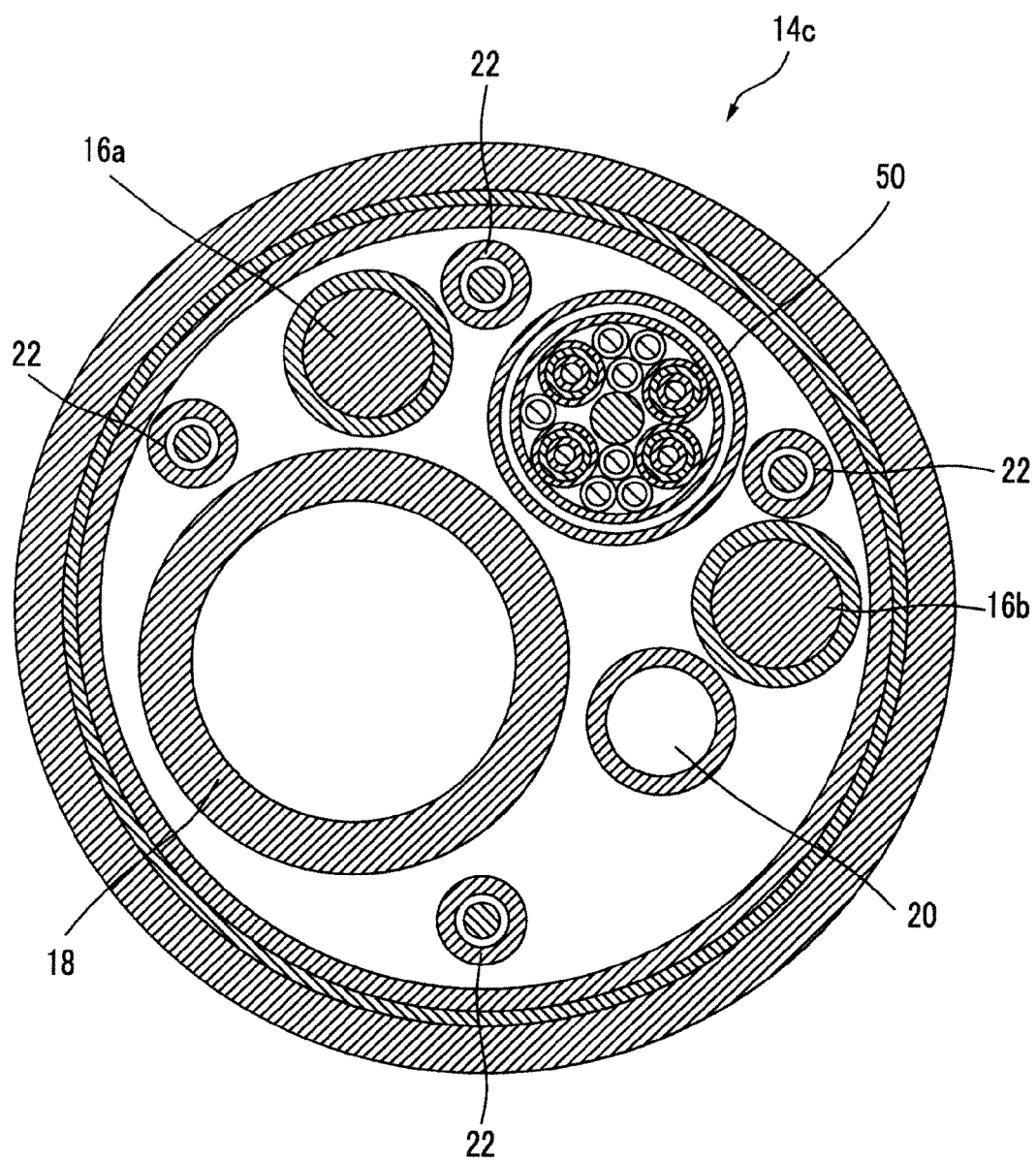
FIG. 2 is a cross-sectional view showing the schematic structure inside a flexible tube portion.

FIG. 2 is a cross-sectional view showing a schematic structure inside the flexible tube portion. As shown in this drawing, light guides 16a and 16b, a forceps channel 18, an air and water supply channel 20, a bundle-wire cable 50, angle wires 22, and the like are accommodated inside the flexible tube portion 14c.

Figure 3:
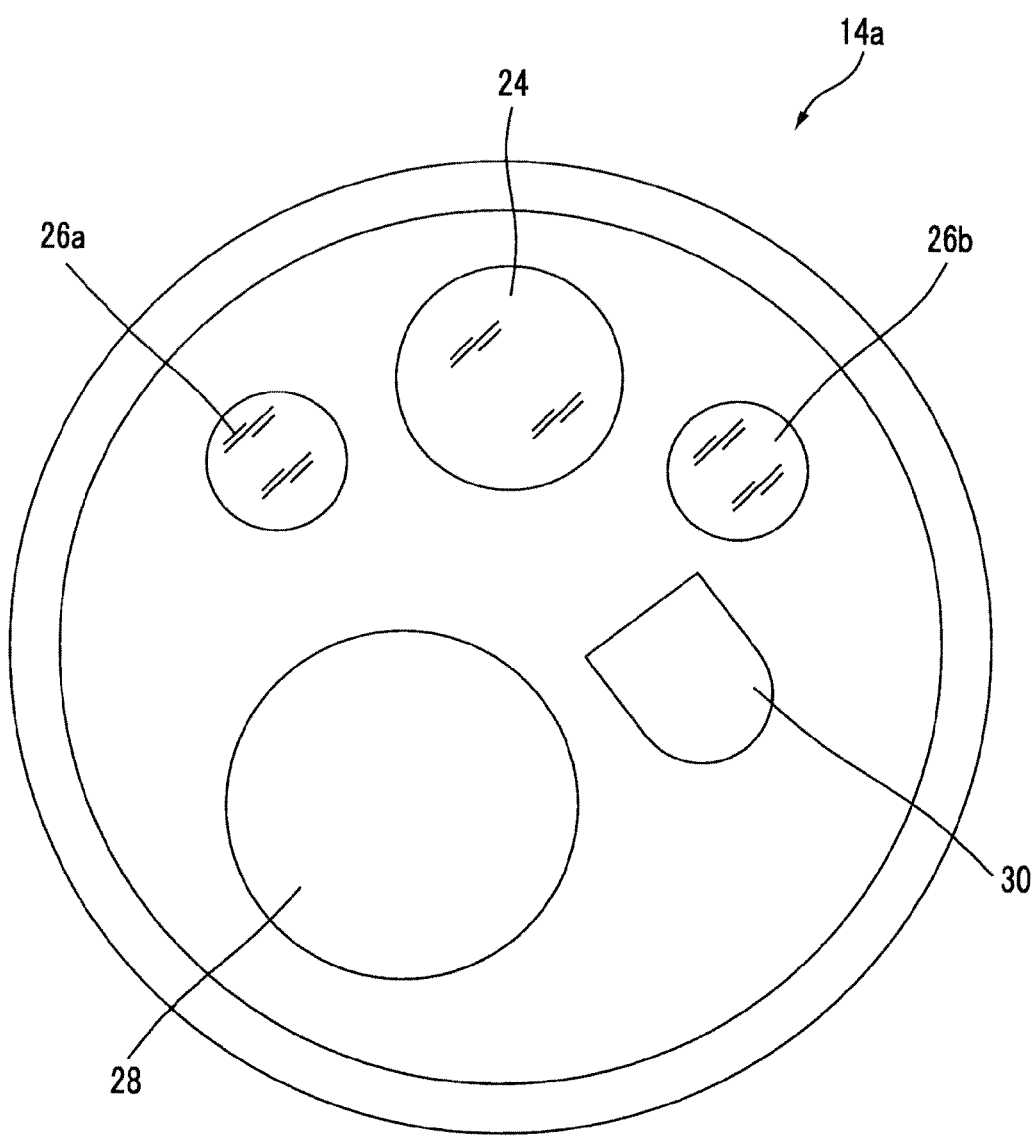
FIG. 3 is a view showing the configuration of a distal end face of an insertion part.

FIG. 3 is a view showing the configuration of a distal end face of the insertion part. As shown in this drawing, the distal end face of the insertion part 14 is provided with an observation window 24, illumination windows 26a and 26b, a forceps outlet 28, an air and water supply nozzle 30, and the like.

The observation window 24 is a window portion for observing the inside of a body cavity, and has an objective optical system 32 disposed therein. Incident image light of an observation region on the objective optical system 32 via the observation window 24 is incident on the light-receiving surface of an imaging element 36 via a prism 34 (refer to FIG. 4). In so doing, an image can be captured within the body cavity.

The illumination windows 26a and 26b are window portions for emitting illumination light, and have illumination optical systems (not shown) disposed therein, respectively. The light guides 16a and 16b are connected to the illumination optical systems, respectively. The light guides 16a and 16b are configured by bundling a number of optical fibers, guide illumination light emitted from the light source device 4 to the illumination optical systems. Incident illumination light to the illumination optical systems via light guides 16a and 16b are radiated toward an observation region from the illumination windows 26a and 26b.

The forceps outlet 28 is an outlet portion of various treatment tools inserted from the forceps inlet 12a provided in the manipulating part 12, and communicates with the forceps channel 18.

The air and water supply nozzle 30 is a nozzle that jets air or washing liquid toward the observation window 24, and is coupled to the air and water supply channel 20. If the air and water supply button 12c of the manipulating part 12 is manipulated, air or washing water that is supplied from an air and water supply device (not shown) built in the light source device 4 is sent to the air and water supply nozzle 30 via the air and water supply channel 20, and is jetted toward the observation window 24.

Figure 4:
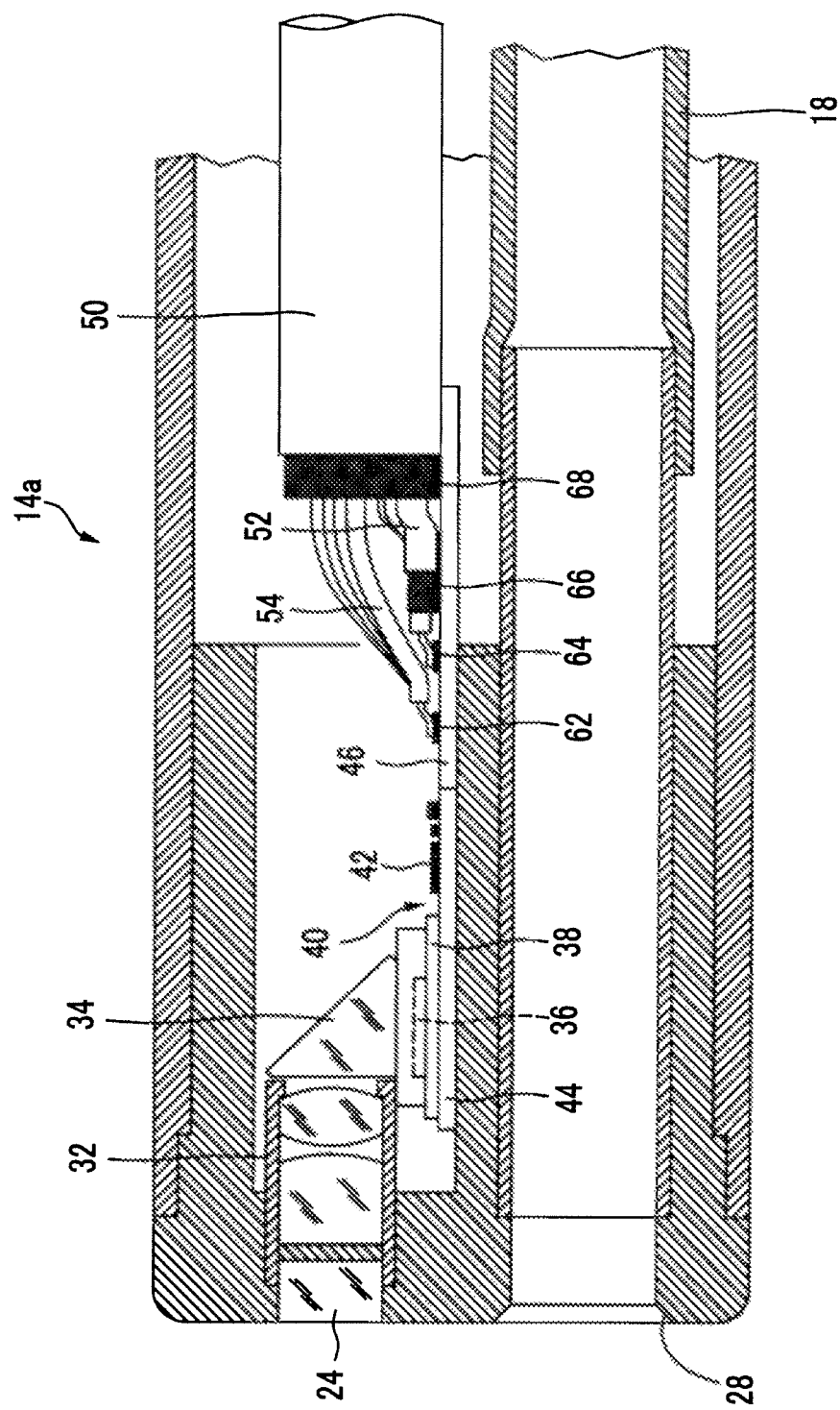
FIG. 4 is a lateral cross-sectional view showing the internal structure of a distal end of the insertion part.

FIG. 4 is a lateral cross-sectional view of the distal end of the insertion part. As described above, the objective optical system 32 is disposed inside the observation window 24. The prism 34 is arranged at the subsequent stage of the objective optical system 32. The imaging element 36 is arranged under the prism 34. The imaging elements 36 (for example, CCD, CMOS, or the like) are loaded onto an imaging element mounting portion 44 of a circuit board 40 via a mount 38.

The circuit board 40 is constituted by a flexible printed circuit board, and has various electronic components 42 besides the imaging element 36 mounted thereon. Additionally, the circuit board 40 is provided with a cable-connecting portion 46 for connecting the bundle-wire cable 50, and has a plurality of connecting terminals (pads) for connecting the bundle-wire cable 50 provided on the top face thereof. This point will be described below. The circuit board 40 is attached to the distal end portion 14a of the insertion part 14 by fixing means (screw or the like) that is not shown.

Here, the configuration of the bundle-wire cable 50 will be described.

Figure 5:
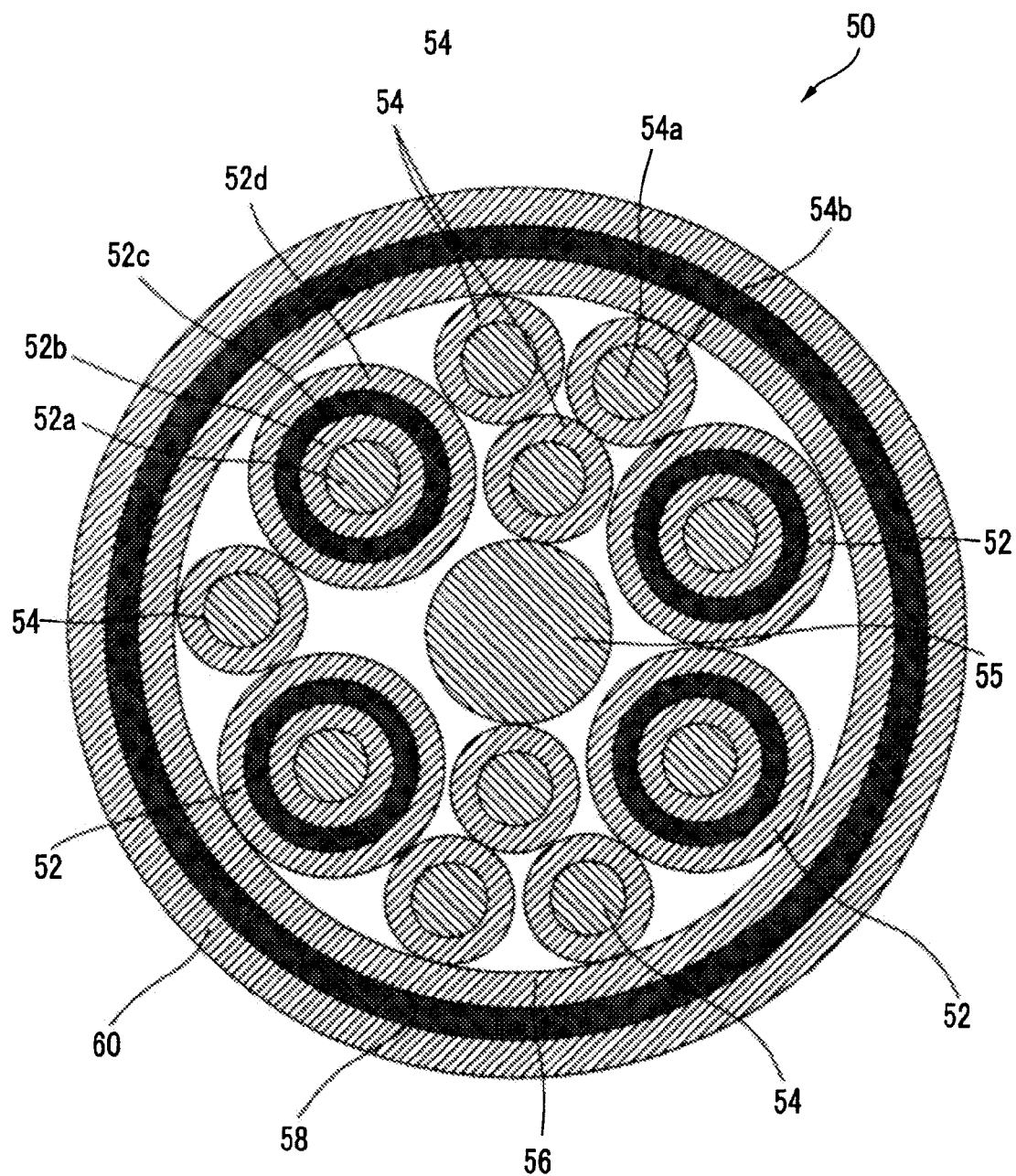
FIG. 5 is a cross-sectional view showing the schematic configuration of a bundle-wire cable.

FIG. 5 is a cross-sectional view showing the schematic configuration of the bundle-wire cable. Additionally, FIG. 6 is a side view of the bundle-wire cable.

Figure 6:
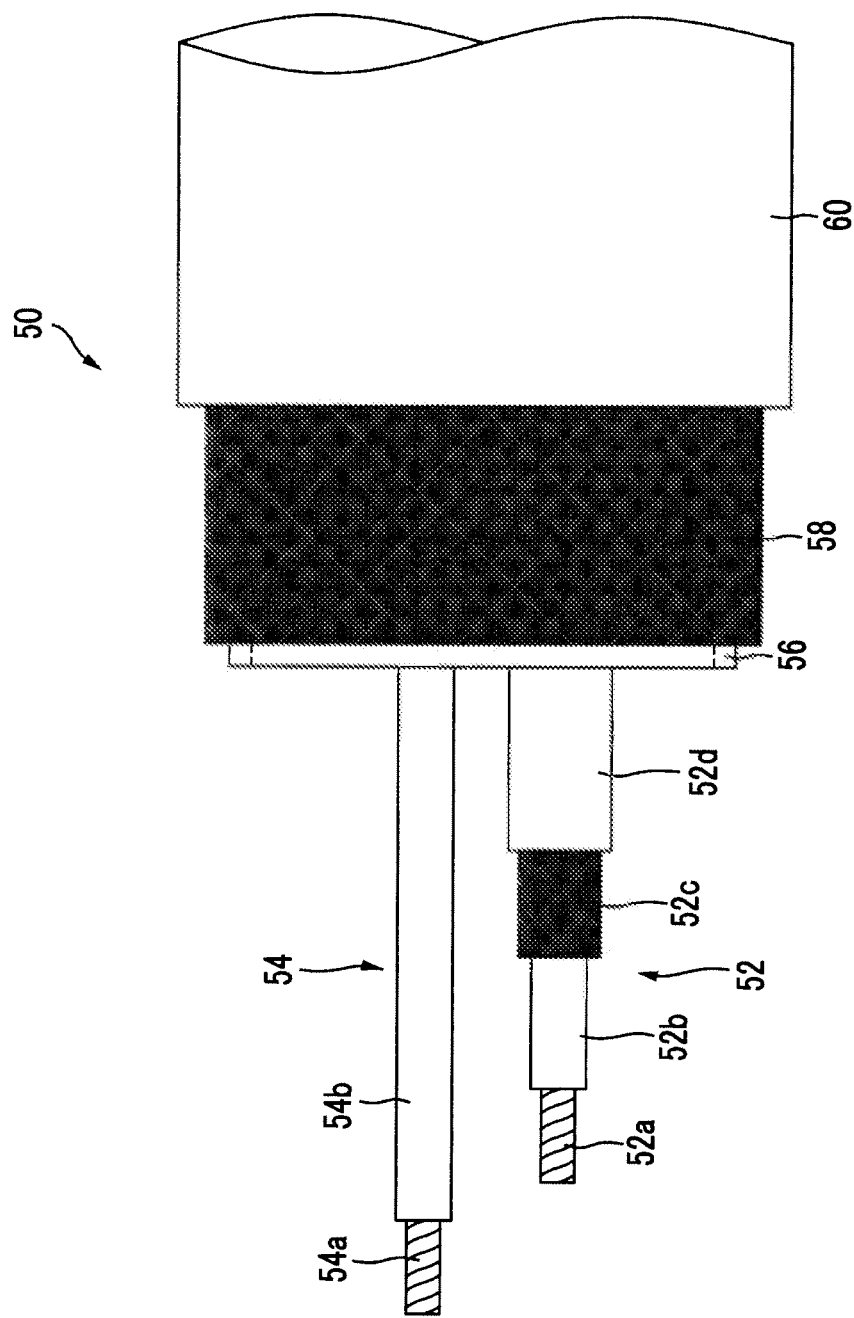
FIG. 6 is a side view of the bundle-wire cable.

As shown in FIGS. 5 and 6, the bundle-wire cable 50 is constituted by bundling a plurality (four in this example) of coaxial cables 52 that are signal lines, a plurality of (seven in this example) single-wire cables 54, and an interposed cord 55 (in addition, in FIG. 6, one coaxial cable 52 and one single-wire cable 54 are illustrated in order to make the configuration easily understood).

The bundle-wire cable 50 is constituted by a tubular bundle-wire insulator 56 that accommodates the plurality of coaxial cables 52 and the plurality of single-wire cables 54 being bundled, a tubular bundle-wire shield 58 that covers the periphery of the bundle-wire insulator 56, and a tubular bundle-wire covering 60 that covers the periphery of the bundle-wire shield 58. The bundle-wire insulator 56 is constituted by an insulator. The bundle-wire shield 58 is configured by knitting a plurality of shielding wires into a tubular shape. The bundle-wire covering 60 is constituted by an insulator.

The coaxial cables 52 are constituted by a coaxial core (inner conductor) 52a, a tubular coaxial insulator 52b that covers the periphery of the coaxial core 52a, a tubular coaxial shield (outer conductor) 52c that covers the periphery of the coaxial insulator 52b, and a tubular coaxial covering 52d that covers the periphery of the coaxial shield 52c. The coaxial core 52a is constituted by a conducting wire. The coaxial insulator 52b is constituted by an insulator. The coaxial shield 52c is constituted by knitting a plurality of shielding wires into a tubular shape. The coaxial covering 52d is constituted by an insulator.

The single-wire cables 54 are constituted by a single-wire core 54a, and a tubular single-wire covering 54b that covers the periphery of the single-wire core 54a. The single-wire core 54a is constituted by a conducting wire, and the single-wire covering 54b is constituted by an insulator.

Figure 7:
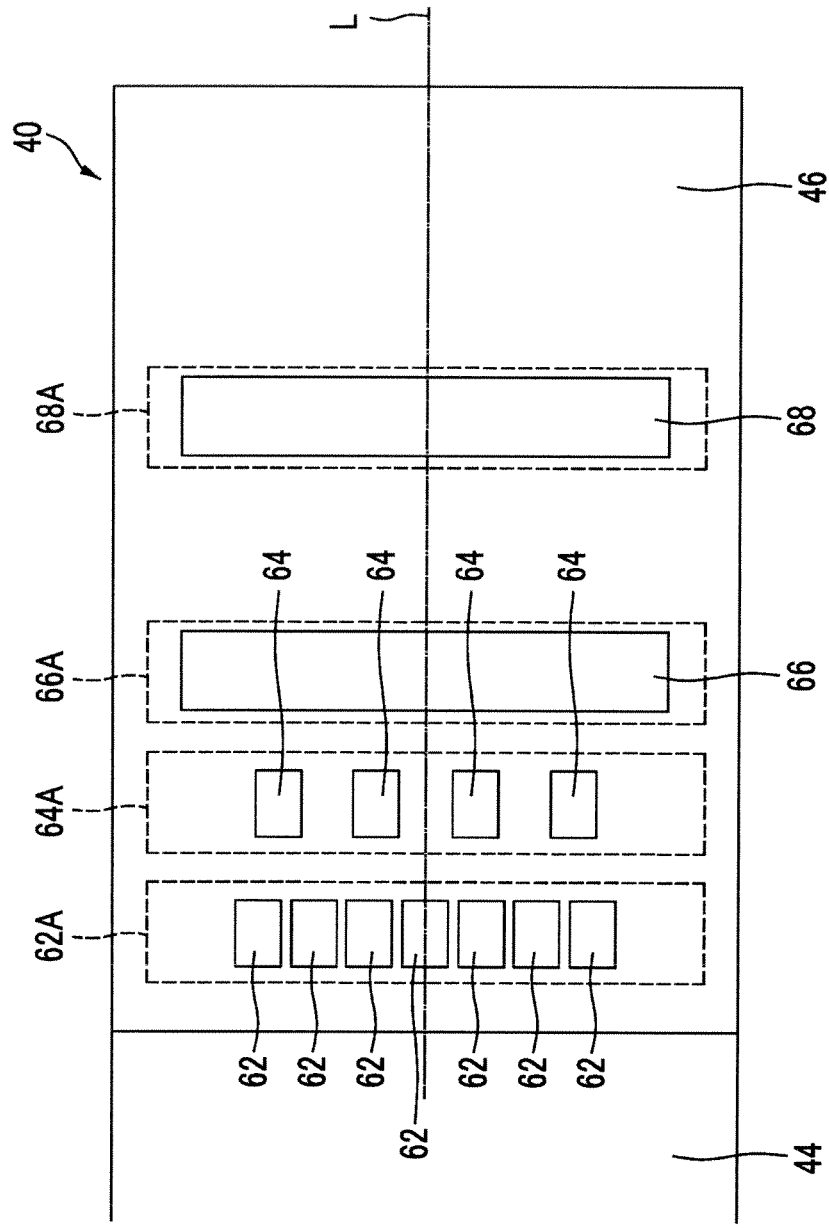
FIG. 7 is a plan view of a cable connecting portion of a circuit board.

FIG. 7 is a plan view of the cable connection of the circuit board. As shown in this drawing, the cable-connecting portion 46 of the circuit board 40 is formed in a rectangular shape, and a top face of the cable-connecting portion 46 is provided with a plurality of single-wire core connecting terminals 62 to which the single-wire cores 54a of the plurality of single-wire cables 54 are connected individually, a plurality of coaxial core connecting terminals 64 to which the coaxial cores 52a of the plurality of coaxial cables 52 are individually connected, a coaxial shield connecting terminal 66 (GND) to which the coaxial shields 52c of the plurality of coaxial cables 52 are connected collectively, and a bundle-wire shield connecting terminal 68 (GND) to which the bundle-wire shield 58 of the bundle-wire cable 50 is connected.

Here, the single-wire core connecting terminals 62 are provided in a single-wire core connecting terminal forming region 62A set on the top face of the cable-connecting portion 46, and the coaxial core connecting terminals 64 are provided in a coaxial core connecting terminal forming region 64A set on the top face of the cable-connecting portion 46. Additionally, the coaxial shield connecting terminal 66 is provided in a coaxial shield connecting terminal forming region 66A set on the top face of the cable-connecting portion 46, and the bundle-wire shield connecting terminal 68 is provided in a bundle-wire shield connecting terminal forming region 68A set on the top face of the cable-connecting portion 46.

The single-wire core connecting terminal forming region 62A, the coaxial core connecting terminal forming region 64A, the coaxial shield connecting terminal forming region 66A, and the bundle-wire shield connecting terminal forming region 68A are all set on the top face of the cable-connecting portion 46, and are arranged in a column at predetermined intervals on the common straight line (L). That is, when the bundle-wire cable 50 is connected, the single-wire core connecting terminal forming region 62A, the coaxial core connecting terminal forming region 64A, the coaxial shield connecting terminal forming region 66A, and the bundle-wire shield connecting terminal forming region 68A are arranged side by side on the straight line (L) along the axis of the bundle-wire cable 50. This enables connection work of all wiring lines to be performed collectively on one-side face of the cable-connecting portion 46 of the circuit board 40, and enables the breadth (width in a direction orthogonal to the axis of the bundle-wire cable 50) of the cable-connecting portion 46 of the circuit board 40 to be suppressed.

Figure 8:
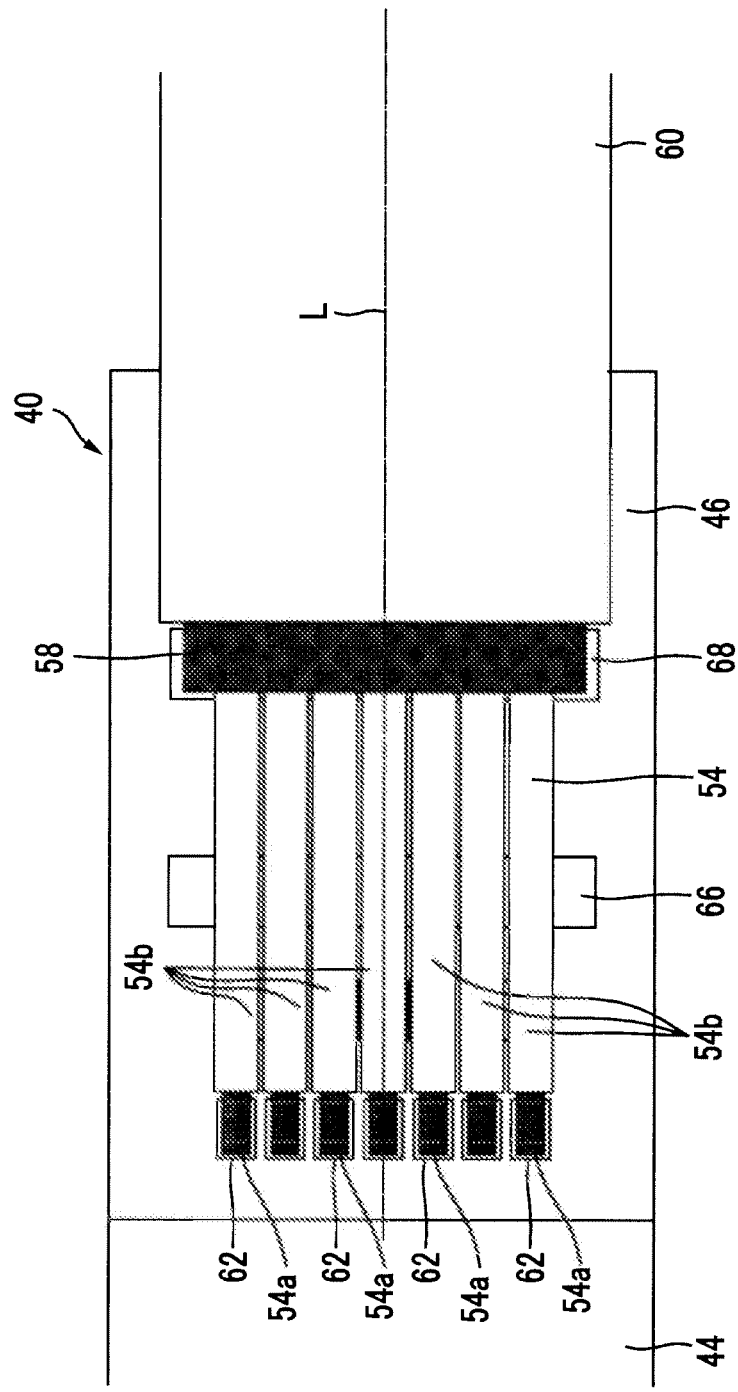
FIG. 8 is a view showing the connection structure of a single-wire cable.

Additionally, in the single-wire core connecting terminal forming region 62A, the respective single-wire core connecting terminals 62 are arranged in parallel in a direction orthogonal to the straight line L, and are arranged symmetrically with respect to the straight line L. Particularly, as shown in FIG. 8, when the single-wire cables 54 are arranged side by side on the cable-connecting portion 46 of the circuit board 40, these single-wire cables are arranged corresponding to the positions of the single-wire cores 54a of the respective single-wire cables 54 (arranged at the same intervals as the arrangement intervals of the single-wire cores 54a of the respective single-wire cables 54). This enables the positions of the respective single-wire cores 54a to be aligned with the forming positions of the respective single-wire core connecting terminals 62 and enables connection working to be performed easily, simply by arranging the respective single-wire cables 54 side by side on the cable-connecting portion 46 during the connection work of the respective single-wire cores 54a.

Figure 9:
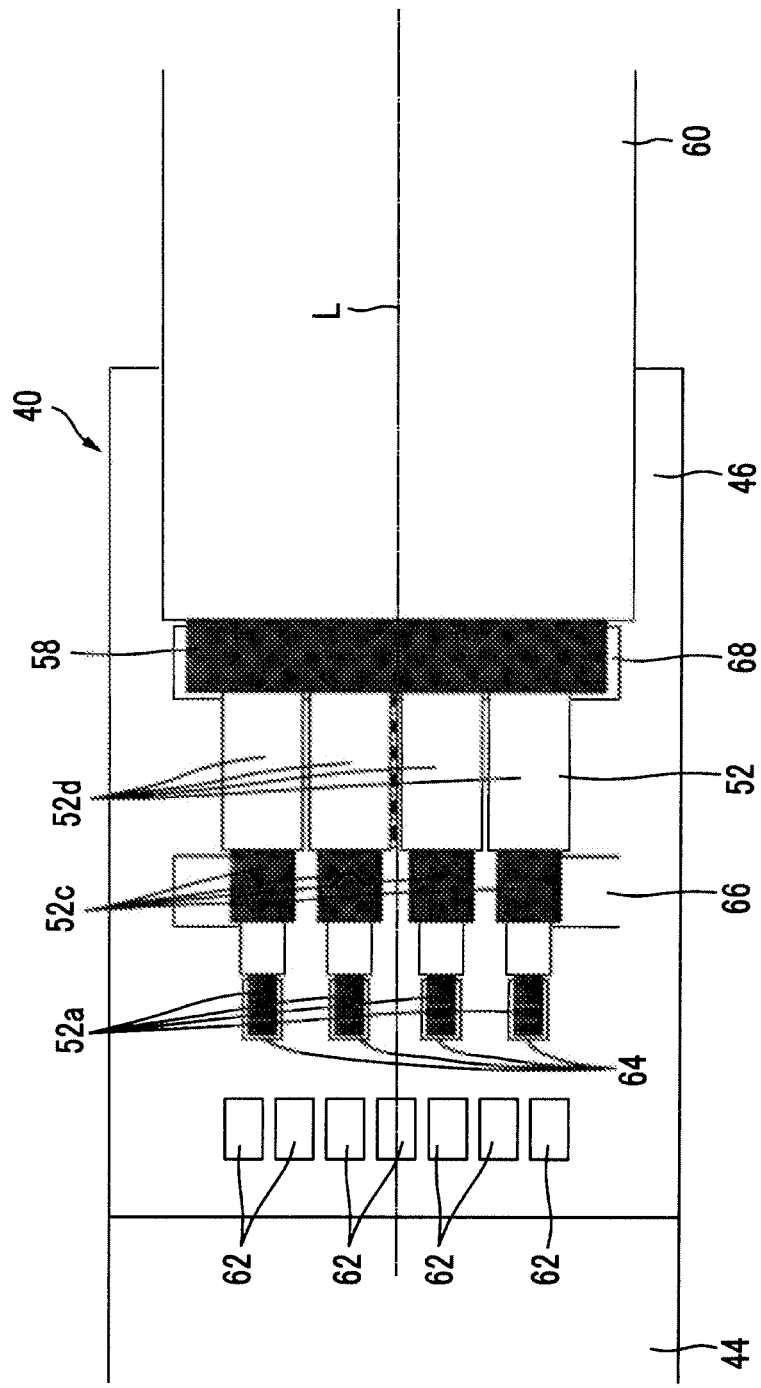
FIG. 9 is a view showing the connection structure of a coaxial cable.

The coaxial core connecting terminals 64, similarly to the single-wire core connecting terminals 62, are also arranged in parallel in the direction orthogonal to the straight line L, and are arranged symmetrically with respect to the straight line L. Particularly, as shown in FIG. 9, when the coaxial cables 52 are arranged side by side on the cable-connecting portion 46 of the circuit board 40, these coaxial cables are arranged corresponding to the positions of the coaxial cores 52a of the respective coaxial cables 52 (arranged at the same intervals as the arrangement intervals of the coaxial cores 52a of the respective coaxial cables 52). This enables the positions of the respective coaxial cores 52a to be aligned with the forming positions of the respective coaxial core connecting terminals 64 and enables connection work to be performed easily, simply by arranging the respective coaxial cables 52 side by side on the cable-connecting portion 46 of the circuit board 40 during the connection work of the respective coaxial cores 52a.

On the other hand, the coaxial shield connecting terminal 66 is formed in a belt shape, and is arranged so as to be orthogonal to the straight line L. Particularly, when the coaxial cables 52 are arranged side by side on the cable-connecting portion 46 of the circuit board 40, these coaxial cables are formed with a breadth such that the coaxial shields 52c of the respective coaxial cables 52 can be placed. This enables the respective coaxial shields 52c to be brought into contact with the coaxial shield connecting terminal 66 and enables connection work to be performed easily, simply by arranging the respective coaxial cables 52 side by side on the cable-connecting portion 46 of the circuit board 40 during the connection work of the respective coaxial shields 52c.

The bundle-wire shield connecting terminal 68, similarly to the coaxial shield connecting terminal 66, is also formed in a belt shape, and is arranged so as to be orthogonal to the straight line L. The bundle-wire shield connecting terminal 68 is formed with a breadth such that at least the bundle-wire shield 58 can come into contact therewith when the bundle-wire cable 50 is placed on the cable-connecting portion 46 of the circuit board 40.

As described above, the single-wire core connecting terminal forming region 62A where the single-wire core connecting terminals 62 are formed, the coaxial core connecting terminal forming region 64A where the coaxial core connecting terminals 64 are formed, the coaxial shield connecting terminal forming region 66A where the coaxial shield connecting terminal 66 is formed, and the bundle-wire shield connecting terminal forming region 68A where the bundle-wire shield connecting terminal 68 is formed are set on the top face of the cable-connecting portion 46 of the circuit board 40 and are arranged in a column on the straight line L. The respective single-wire core connecting terminals 62 formed in the single-wire core connecting terminal forming region 62A and the coaxial core connecting terminals 64 formed in the coaxial core connecting terminal forming region 64A are arranged in parallel in the direction orthogonal to the straight line L, and are arranged symmetrically with respect to the straight line L. Additionally, the coaxial shield connecting terminal 66 formed in the coaxial shield connecting terminal forming region 66A and the bundle-wire shield connecting terminal 68 formed in the bundle-wire shield connecting terminal forming region 68A are formed in a belt shape, and are arranged so as to be orthogonal to the straight line L.

Here, the single-wire core connecting terminal forming region 62A, the coaxial core connecting terminal forming region 64A, the coaxial shield connecting terminal forming region 66A, and the bundle-wire shield connecting terminal forming region 68A, which are arranged in a column along the straight line L, are arranged closely as possible in the direction of the straight line L. This can shorten the longitudinal width (width in the direction along the straight line L) of the cable-connecting portion 46 of the circuit board 40. Additionally, the shields can be arranged closely, and the shielding effect can be enhanced.

Additionally, the longitudinal width of the respective connecting terminals is set to such a width that the respective cores or shields can be reliably connected.

In a case where the bundle-wire cable 50 is connected, covering peeling processing is performed in conformity with the positions (lengths) of the connecting terminals formed in each region. The connection method will be outlined below.

FIGS. 10A to 10D are views showing a connection procedure of the bundle-wire cable to the circuit board.

Figure 10A:
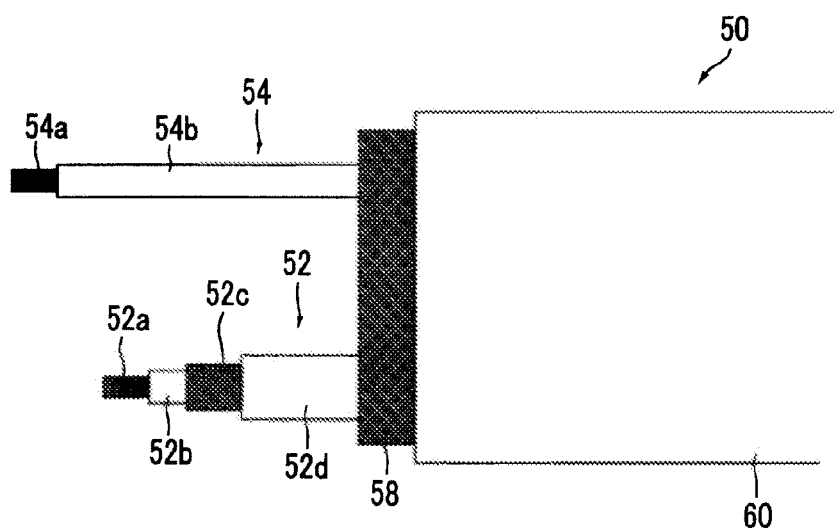
FIGS. 10A to 10D are views showing a connection procedure of the bundle-wire cable to the circuit board.

First, as shown in FIG. 10A, covering peeling processing of the respective cables is performed. In this case, the pullout amounts of the cables, the exposure amounts of the cores and the shields, and the like are adjusted in conformity with the positions of the connecting terminals formed in the cable-connecting portion 46 of the circuit board 40. In this case, the pullout amounts of the respective cables, the exposure amounts of the cores and the shields, and the like are adjusted with reference to the bundle-wire shield 58.

Specifically, first, the bundle-wire shield 58 is exposed in conformity with the longitudinal width of the bundle-wire shield connecting terminal 68.

Next, the coaxial cables 52 are pulled out and the coaxial cores 52a and the coaxial shields 52c are exposed so as to reach the coaxial core connecting terminals 64 and the coaxial shield connecting terminal 66, with reference to the distal end of the bundle-wire shield 58. In this case, the coaxial cores 52a are exposed in conformity with the longitudinal width of the coaxial core connecting terminals 64. Similarly, the coaxial shields 52c are exposed in conformity with the longitudinal width of the coaxial shield connecting terminal 66.

Similarly to the coaxial cables 52, the single-wire cables 54 are pulled out and the single-wire cores 54a are exposed so as to reach the single-wire core connecting terminals 62 with reference to the distal end of the bundle-wire shield 58. In this case, the single-wire cores 54a are exposed in conformity with the longitudinal width of the single-wire core connecting terminals 62.

In addition, in the example shown in FIG. 10A, one single-wire cable 54 and one coaxial cable 52 are described in order to make the state of the respective cables easily understood.

Figure 10B:
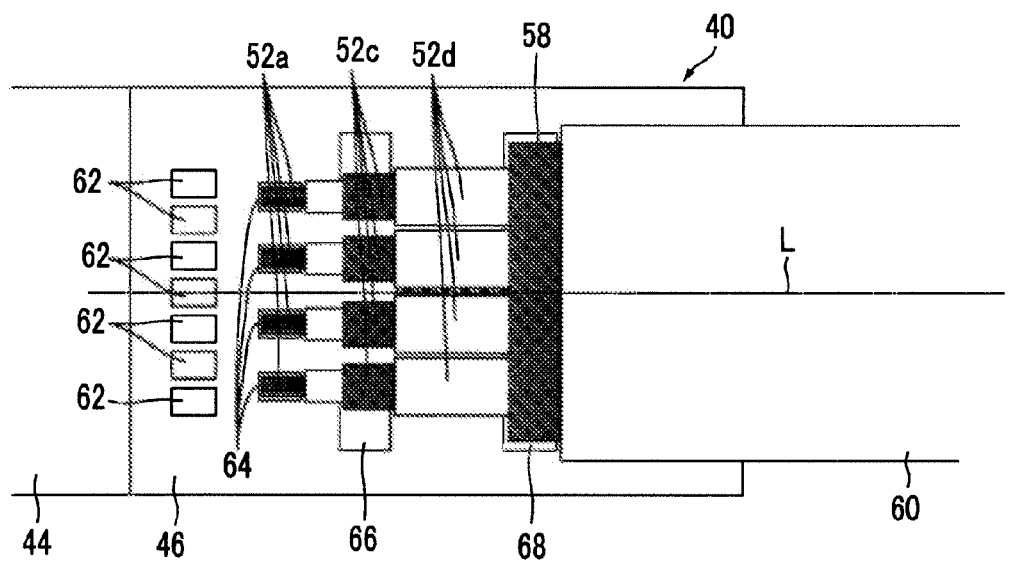

Next, as shown in FIG. 10B, the bundle-wire cable 50 is placed on the cable-connecting portion 46 of the circuit board 40 in conformity with the position of the bundle-wire shield 58 and the bundle-wire shield connecting terminal 68. Then, the bundle-wire shield 58 is connected to the bundle-wire shield connecting terminal 68. The connection is performed by, for example, laser welding or soldering.

Figure 10C:
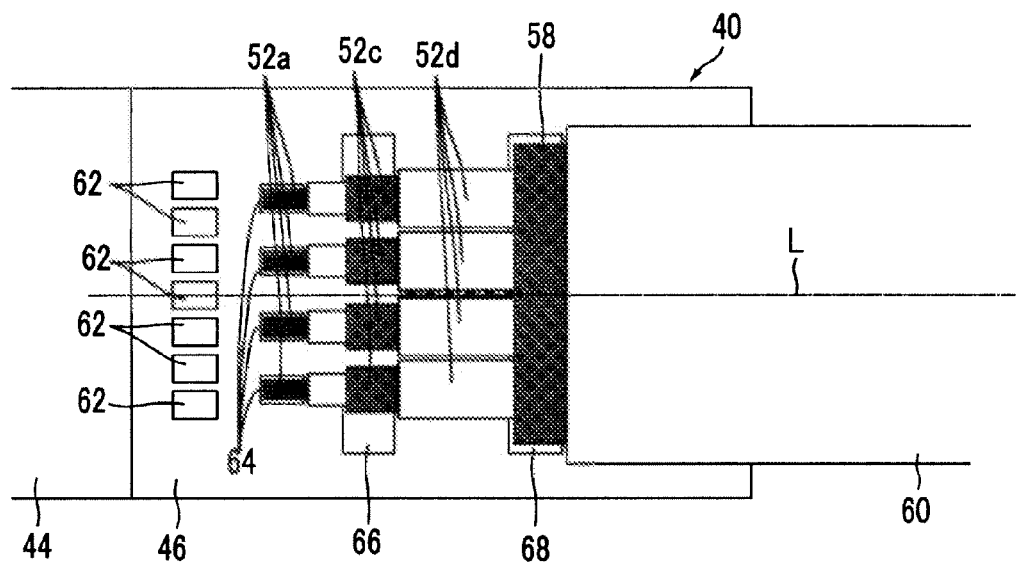

Next, as shown in FIG. 10C, the coaxial cables 52 are placed on the cable-connecting portion 46 of the circuit board 40 so that the positions of the coaxial cores 52a of the coaxial cables 52 coincide with the positions of the coaxial core connecting terminals 64 each other. In addition, in this drawing, the description of the single-wire cables 54 is omitted for convenience of description.

Here, as described above, the coaxial cables 52 are pulled out while their lengths are adjusted so that the positions of the coaxial cores 52a coincide with the positions of the coaxial core connecting terminals 64. Additionally, the coaxial core connecting terminals 64 are also adjusted and formed so that the coaxial cores 52a of the respective coaxial cables 52 are located when the coaxial cables 52 are placed side by side on the cable-connecting portion 46 of the circuit board 40. Accordingly, the coaxial cores 52a can be located on the corresponding coaxial core connecting terminals 64 simply by placing the respective coaxial cables 52 side by side on the cable-connecting portion 46 of the circuit board 40.

Additionally, since the coaxial shields 52c are processed so as to be exposed corresponding to the coaxial shield connecting terminal 66, the coaxial shields 52c of the respective coaxial cables 52 can be located on the coaxial shield connecting terminal 66 simply by placing the respective coaxial cables 52 side by side on the cable-connecting portion 46 of the circuit board 40.

In this way, the respective coaxial cables 52 are placed side by side on the cable-connecting portion 46 of the circuit board 40, the coaxial cores 52a are located on the coaxial core connecting terminals 64, and the coaxial shields 52c are placed on the coaxial shield connecting terminal 66. Then, the coaxial cores 52a are connected to the coaxial core connecting terminals 64. Additionally, the coaxial shields 52c are connected to the coaxial shield connecting terminal 66. The connection is performed by, for example, laser welding or soldering.

The connection of the coaxial cables 52 is completed by the above.

Figure 10D:
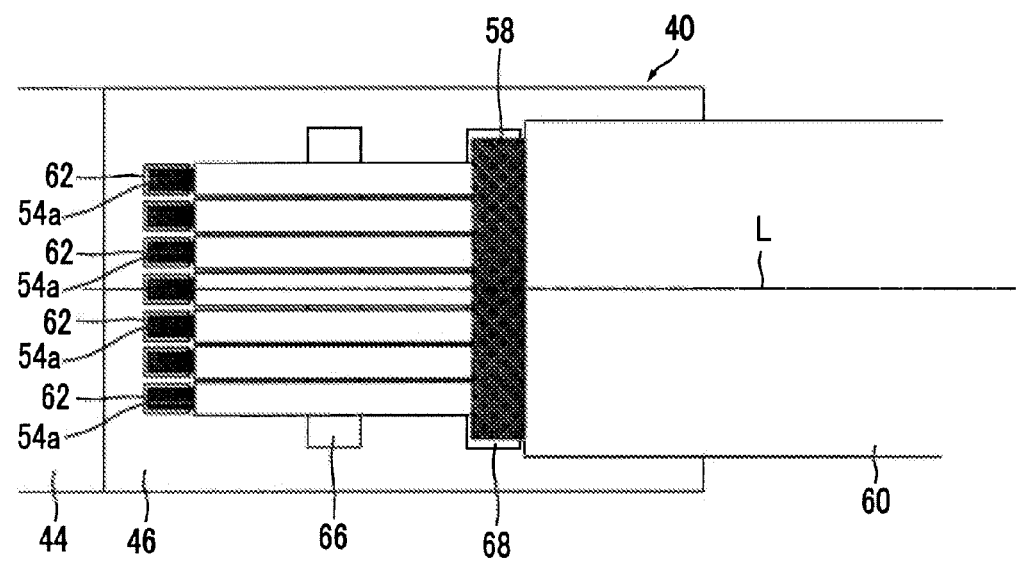

Next, as shown in FIG. 10D, the single-wire cables 54 are placed on the cable-connecting portion 46 of the circuit board 40 so that the positions of the single-wire cores 54a of the single-wire cables 54 coincide with the positions of the single-wire core connecting terminals 62. In addition, in this drawing, the description of the coaxial cables 52 is omitted for convenience of description.

Here, as described above, the single-wire cables 54 are pulled out while their lengths are adjusted so that the positions of the single-wire cores 54*a* coincide with the positions of the single-wire core connecting terminals 62. Additionally, the single-wire core connecting terminals 62 are also adjusted and formed so that the single-wire cores 54*a* of the respective single-wire cables 54 are located when the single-wire cables 54 are placed side by side on the cable-connecting portion 46. Accordingly, the single-wire cores 54*a* can be located on the corresponding single-wire core connecting terminals 62 simply by placing the respective single-wire cables 54 side by side on the cable-connecting portion 46 of the circuit board 40.

After the single-wire cores 54*a* are located on the single-wire core connecting terminals 62, the single-wire cores 54*a* are connected to the single-wire core connecting terminals 62. The connection is performed by, for example, laser welding or soldering.

The bundle-wire cable 50 is connected to the cable-connecting portion 46 of the circuit board 40 through a series of the above processes.

The connection work can be performed efficiently by adopting the structure in which the respective cables of the bundle-wire cable are connected together on the common plane of the cable-connecting portion 46 of the circuit board 40. Additionally, the longitudinal width of the cable-connecting portion 46 of the circuit board 40 can be suppressed, and the circuit board can be miniaturized, by arranging the firming regions of the respective connecting terminals side by side back and forth in the axial direction of the bundle-wire cable 50. Moreover, the cores and shields of the respective coaxial cables 52 can be connected together close to each other, and the shielding effect can be improved. Additionally, the alignment between the respective cores and the respective connecting terminals and the alignment between the respective shields and the respective connecting terminals can be performed simply by placing the respective cables on the cable-connecting portion 46 of the circuit board 40, and connection work can be performed easily.

In addition, in the above embodiment, the respective connecting terminal forming regions are formed in the order of the single-wire core connecting terminal forming region 62A, the coaxial core connecting terminal forming region 64A, the coaxial shield connecting terminal forming region 66A, and the bundle-wire shield connecting terminal forming region 68A from the distal end side in the axial direction of the bundle-wire cable 50. However, the order of the single-wire core connecting terminal forming region 62A, the coaxial core connecting terminal forming region 64A, and the coaxial shield connecting terminal forming region 66A is not limited thereto. For example, as shown in FIG. 11, the coaxial core connecting terminal forming region 64A, the coaxial shield connecting terminal forming region 66A, and the single-wire core connecting terminal forming region 62A can be formed in this order from the distal end side in the axial direction of the bundle-wire cable 50.

Figure 12:
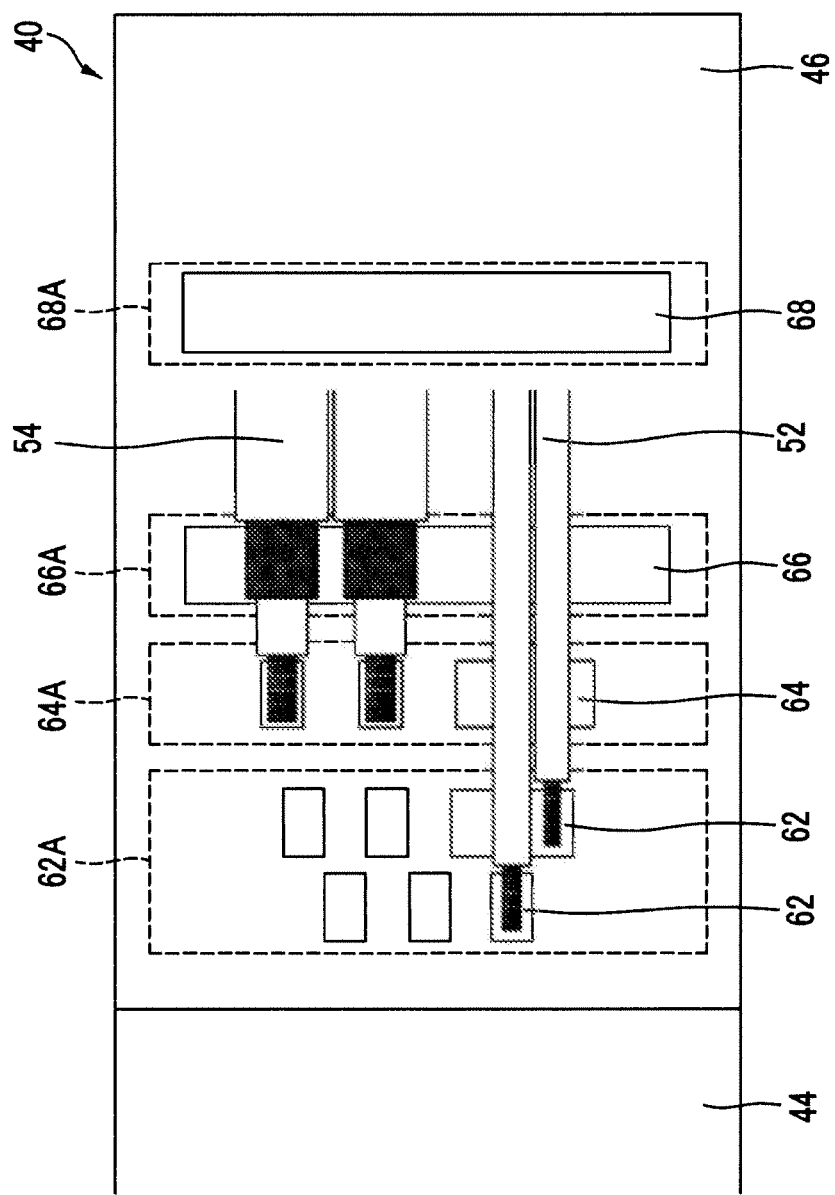
FIG. 12 is a view showing still another example of an array of connecting terminals.

Additionally, the above embodiment has the configuration in which the single-wire core connecting terminals 62 that are formed plurally are arranged in parallel to the direction orthogonal to the straight line L. However, the single-wire core connecting terminals are not necessarily arranged on the common straight line (on a straight line orthogonal to the straight line L). As shown in FIG. 12, a configuration in which the single-wire core connecting terminals are arranged so as to shift back and forth alternately (staggered arrangement) may also be adopted. This is also similar to the coaxial core connecting terminals 64.

However, by adopting a configuration in which the coaxial core connecting terminals are arranged in parallel to the direction orthogonal to the straight line L, the longitudinal width of the cable-connecting portion 46 of the circuit board 40 can be suppressed, and the covering peeling processing of the cable and connection work can also be performed easily. Additionally, the shield can be brought close to each other, and the shielding effect can be enhanced.

Additionally, it is preferable to provide the cable-connecting portion 46 of the circuit board 40 with a fixing portion (bundle-wire covering connecting portion) that fixes the bundle-wire covering 60 of the bundle-wire cable 50. This can further enhance the strength of the cable-connecting portion. As the structure in which the bundle-wire covering 60 of the bundle-wire cable 50 is fixed, for example, a structure may be adopted in which the distal end of the bundle-wire covering 60 of the union cable 50 is positioned and fixed at a predetermined position of the cable-connecting portion 46 (positioned at and fixed to a predetermined fixing portion) and sealed and fixed with resin. In addition, a structure in which the bundle-wire covering 60 of the bundle-wire cable 50 is fixed by a clamp or fixed by caulking can be adopted.

Additionally, in the present embodiment, the circuit board 40 on which the imaging element 36 is mounted, and a cable-connecting board 46 are formed so as to be separated from each other. However, these boards can be formed integrally. However, connection work of the cables can be made easier by separately forming the cable-connecting board 46 as in the present embodiment.

Figure 13:
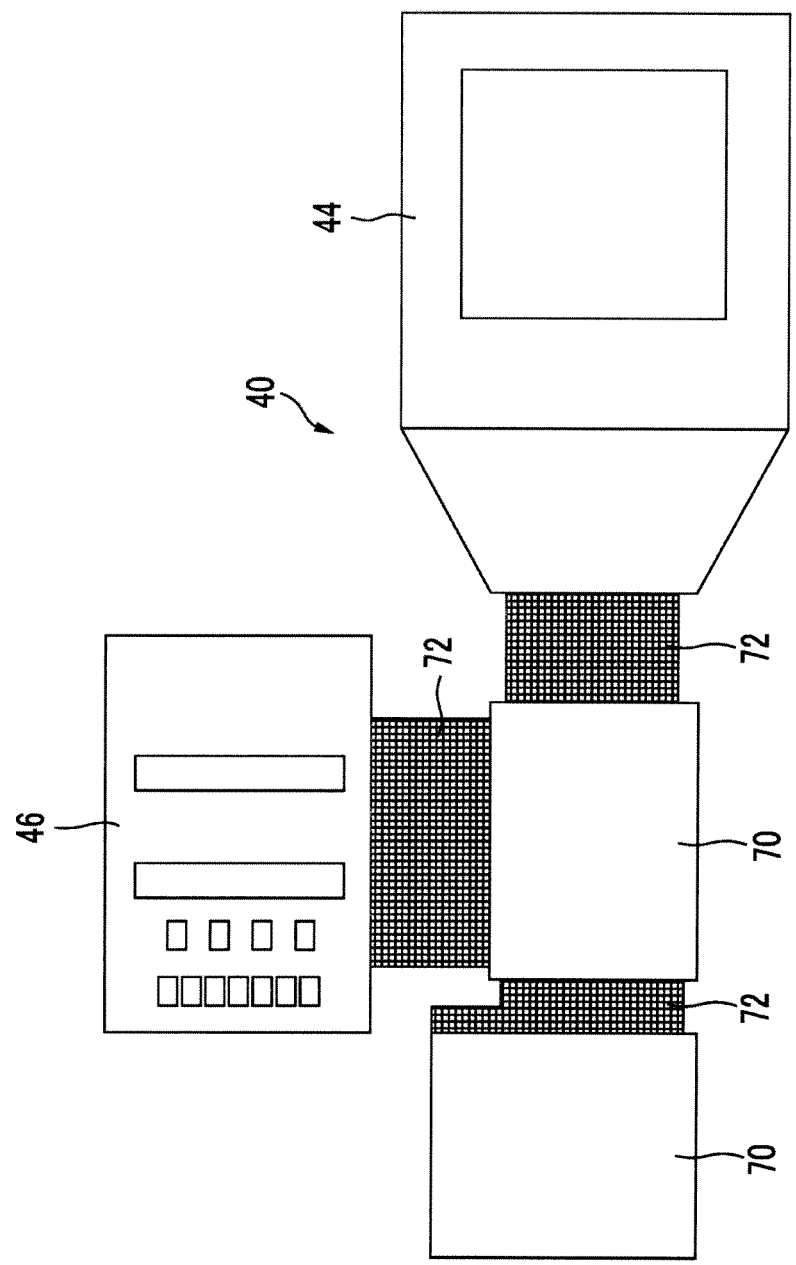
FIG. 13 is a view showing a still further example of an array of connecting terminals.
Figure 14:
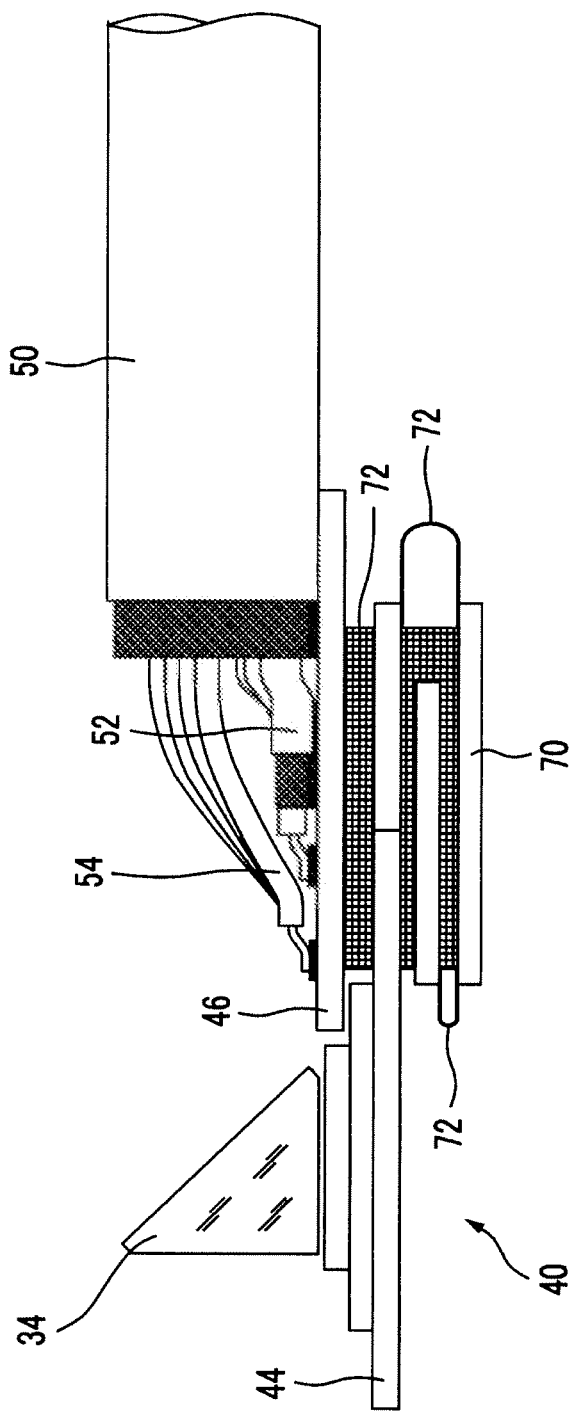
FIG. 14 is a view showing a still further example of an array of connecting terminals.

Additionally, the structure where the respective cables of the bundle-wire cable 50 are connected on the common plane of the circuit board 40 is shown in the present embodiment. However, as shown in FIGS. 13 and 14, a structure that the circuit board 40 constituted by a flexible printed circuit board is folded back, and is accommodated in the distal end portion 14*a* of the insertion part 14 can be adopted. In the example shown in this drawing, the circuit board 40 is constituted by a cable-connecting portion 46, an imaging element mounting portion 44, and other electronic component mounting portions 70, and the respective portion are coupled together by the bendable portion 72 so as to be capable of being folded back. The distal end of the insertion part 14 can be miniaturized by such a foldable configuration.

In addition, in the present embodiment, the case where the bundle-wire cable is connected to the board on which the imaging element is mounted has been described as an example. However, even in a case where the bundle-wire cable is connected to other circuit boards, the invention can be similarly applied.

Additionally, in the present invention, one shield (bundle-wire shield) of the bundle-wire cable 50 is configured. However, multiple shields (for example, double shields) can also be configured (for example, shields are further arranged around the bundle-wire covering, and the periphery of the covering is covered with an insulator).

What is claimed is:

1. An endoscope comprising:
   an insertion part;
   a circuit board arranged in a distal end of the insertion part and having a single wire connecting terminal forming region, a coaxial core connecting terminal forming region, a coaxial shield connecting terminal forming region, and a bundle-wire shield connecting terminal forming region;
   a bundle-wire cable including a plurality of single-wire cables that are bundled together, a plurality of coaxial cables that are bundled together along with the plurality of single-wire cables, a bundle-wire shield that covers the periphery of the plurality of the single-wire cables and the plurality of coaxial cables that are bundled together, and a bundle-wire covering that covers the periphery of the bundle-wire shield, arranged within the insertion part, and connected to the circuit board;

a plurality of single wire connecting terminals provided in the single wire connecting terminal forming region and having cores of the plurality of single-wire cables individually connected to the plurality of single wire connecting terminals;

a plurality of coaxial core connecting terminals provided in the coaxial core connecting terminal forming region and having cores of the plurality of coaxial cables individually connected to the plurality of coaxial core connecting terminals;

a coaxial shield connecting terminal provided in the coaxial shield connecting terminal forming region and having shields of the plurality of the coaxial cables connected to the coaxial shield connecting terminal; and a bundle-wire shield connecting terminal provided in the bundle-wire shield connecting terminal forming region and having the bundle-wire shield connected to the bundle-wire shield connecting terminal, wherein the single wire connecting terminal forming region, the coaxial core connecting terminal forming region, the coaxial shield connecting terminal forming region, and the bundle-wire shield connecting terminal forming region are arranged in a common plane, and are arranged side by side in a column at predetermined intervals on a common straight line.

2. The endoscope according to claim 1,
wherein the plurality of single wire connecting terminals are arranged in parallel at predetermined intervals in a direction orthogonal to the straight line and are arranged symmetrically with respect to the straight line, and the plurality of coaxial core connecting terminals are arranged in parallel at predetermined intervals in the direction orthogonal to the straight line and are arranged symmetrically with respect to the straight line.

3. The endoscope according to claim 2,
wherein the plurality of single wire connecting terminals are arranged at the same intervals as the arrangement intervals of cores of the respective single-wire cables when the plurality of single-wire cables are placed side by side on the circuit board, and the plurality of coaxial core connecting terminals are arranged at the same intervals as the arrangement intervals of cores of the coaxial cables when the plurality of coaxial cables are placed side by side on the circuit board.

4. The endoscope according to claim 3,
wherein the coaxial shield connecting terminal is provided in a belt shape in the direction orthogonal to the straight line, and the bundle-wire shield connecting terminal is provided in a belt shape in the direction orthogonal to the straight line.

5. The endoscope according to claim 4,
wherein the circuit board has a bundle-wire covering connecting portion that connects the bundle-wire covering.

6. The endoscope according to claim 4,
wherein the single wire connecting terminal forming region, the coaxial core connecting terminal forming region, the coaxial shield connecting terminal forming region, and the bundle-wire shield connecting terminal forming region are arranged in a column at predetermined intervals on the straight line in this order from a distal end side of the insertion part.

7. The endoscope according to claim 4,
wherein the circuit board is constituted by a flexible printed circuit board, and a cable connecting portion where the single wire connecting terminal forming region, the coaxial core connecting terminal forming region, the coaxial shield connecting terminal forming region, and the bundle-wire shield connecting terminal forming region are provided, and an electronic component mounting portion where electronic components are mounted are formed, and are adapted so as to be capable of being folded back.

8. The endoscope according to claim 3,
wherein the circuit board has a bundle-wire covering connecting portion that connects the bundle-wire covering.

9. The endoscope according to claim 3,
wherein the single wire connecting terminal forming region, the coaxial core connecting terminal forming region, the coaxial shield connecting terminal forming region, and the bundle-wire shield connecting terminal forming region are arranged in a column at predetermined intervals on the straight line in this order from a distal end side of the insertion part.

10. The endoscope according to claim 3,
wherein the circuit board is constituted by a flexible printed circuit board, and a cable connecting portion where the single wire connecting terminal forming region, the coaxial core connecting terminal forming region, the coaxial shield connecting terminal forming region, and the bundle-wire shield connecting terminal forming region are provided, and an electronic component mounting portion where electronic components are mounted are formed, and are adapted so as to be capable of being folded back.

11. The endoscope according to claim 2,
wherein the coaxial shield connecting terminal is provided in a belt shape in the direction orthogonal to the straight line, and the bundle-wire shield connecting terminal is provided in a belt shape in the direction orthogonal to the straight line.

12. The endoscope according to claim 11,
wherein the circuit board has a bundle-wire covering connecting portion that connects the bundle-wire covering.

13. The endoscope according to claim 11,
wherein the single wire connecting terminal forming region, the coaxial core connecting terminal forming region, the coaxial shield connecting terminal forming region, and the bundle-wire shield connecting terminal forming region are arranged in a column at predetermined intervals on the straight line in this order from a distal end side of the insertion part.

14. The endoscope according to claim 11,
wherein the circuit board is constituted by a flexible printed circuit board, and a cable connecting portion where the single wire connecting terminal forming region, the coaxial core connecting terminal forming region, the coaxial shield connecting terminal forming region, and the bundle-wire shield connecting terminal forming region are provided, and an electronic component mounting portion where electronic components are mounted are formed, and are adapted so as to be capable of being folded back.

15. The endoscope according to claim 2,
wherein the circuit board has a bundle-wire covering connecting portion that connects the bundle-wire covering.

16. The endoscope according to claim 2,
wherein the single wire connecting terminal forming region, the coaxial core connecting terminal forming region, the coaxial shield connecting terminal forming region, and the bundle-wire shield connecting terminal forming region are arranged in a column at predetermined intervals on the straight line in this order from a distal end side of the insertion part.

17. The endoscope according to claim 2,
wherein the circuit board is constituted by a flexible printed circuit board, and a cable connecting portion where the single wire connecting terminal forming region, the coaxial core connecting terminal forming region, the coaxial shield connecting terminal forming region, and the bundle-wire shield connecting terminal forming region are provided, and an electronic component mounting portion where electronic components are mounted are formed, and are adapted so as to be capable of being folded back.

18. The endoscope according to claim 1,
wherein the circuit board has a bundle-wire covering connecting portion that connects the bundle-wire covering.

19. The endoscope according to claim 1,
wherein the single wire connecting terminal forming region, the coaxial core connecting terminal forming region, the coaxial shield connecting terminal forming region, and the bundle-wire shield connecting terminal forming region are arranged in a column at predetermined intervals on the straight line in this order from a distal end side of the insertion part.

20. The endoscope according to claim 1,
wherein the circuit board is constituted by a flexible printed circuit board, and a cable connecting portion where the single wire connecting terminal forming region, the coaxial core connecting terminal forming region, the coaxial shield connecting terminal forming region, and the bundle-wire shield connecting terminal forming region are provided, and an electronic component mounting portion where electronic components are mounted are formed, and are adapted so as to be capable of being folded back.

* * * * *